US009877959B2

(12) United States Patent
Yoon et al.

(10) Patent No.: US 9,877,959 B2
(45) Date of Patent: Jan. 30, 2018

(54) PHARMACEUTICAL COMPOSITION CONTAINING PALONOSETRON

(71) Applicant: SAMYANG BIOPHARMACEUTICALS CORPORATION, Seoul (KR)

(72) Inventors: Hye-Jeong Yoon, Daejeon (KR); Sang-Jun Lee, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 15/107,503

(22) PCT Filed: Dec. 22, 2014

(86) PCT No.: PCT/KR2014/012644
§ 371 (c)(1),
(2) Date: Jun. 23, 2016

(87) PCT Pub. No.: WO2015/099381
PCT Pub. Date: Jul. 2, 2015

(65) Prior Publication Data
US 2016/0317524 A1    Nov. 3, 2016

(30) Foreign Application Priority Data

Dec. 23, 2013 (KR) .................. 10-2013-0161890
Dec. 22, 2014 (KR) .................. 10-2014-0186039

(51) Int. Cl.
| A61K 31/473 | (2006.01) |
|---|---|
| A61K 9/00 | (2006.01) |
| A61K 47/12 | (2006.01) |
| A61K 47/26 | (2006.01) |
| A61K 9/19 | (2006.01) |

(52) U.S. Cl.
CPC .......... *A61K 31/473* (2013.01); *A61K 9/0019* (2013.01); *A61K 47/12* (2013.01); *A61K 47/26* (2013.01); *A61K 9/19* (2013.01)

(58) Field of Classification Search
CPC .... A61K 31/473; A61K 9/0019; A61K 47/26; A61K 47/12; A61K 9/08; A61K 9/19
See application file for complete search history.

(56) References Cited

U.S. PATENT DOCUMENTS

| 5,071,880 A | 12/1991 | Sugo |
|---|---|---|
| 5,202,333 A | 4/1993 | Berger |
| 7,960,424 B2 | 6/2011 | Calderari |
| 2004/0176237 A1* | 9/2004 | Ott .................. C03C 3/091 |
| | | 501/66 |
| 2008/0152704 A1 | 6/2008 | Bonadeo |
| 2010/0048607 A1 | 2/2010 | Kocherlakota |
| 2012/0238596 A1* | 9/2012 | Kocherlakota ...... A61K 9/0019 |
| | | 514/296 |

FOREIGN PATENT DOCUMENTS

| CN | 101007004 | 8/2007 |
|---|---|---|
| JP | 11-35068 | 2/1999 |
| JP | 2004-515529 | 5/2004 |
| JP | 2006-516583 | 7/2006 |
| JP | 2008-280430 | 11/2008 |
| JP | 2009-506030 | 2/2009 |
| JP | 2009-507933 | 2/2009 |
| KR | 10-1113084 | 1/2012 |
| KR | 10-1113087 | 1/2012 |
| WO | 2002-017399 | 2/2002 |
| WO | 2013-179514 | 12/2013 |

OTHER PUBLICATIONS

Transmission from Master of Drug formulation, 2nd volume, "Design of Parenteral administration formulation and preparation method therefor", May 20, 2013,(related parts: Fig. 4, Table. 4).
Lawrence A Trissel et al., The Annals of Pharmacotherapy, "Physical and Chemical Stability of Palonosetron HCI in 4 Infusion Solutions" Oct. 2004, vol. 38, pp. 1608-1611.
T.C. Kupie et al., American Journal of Health-System Pharmacy., "Physical and chemical stability of palonosetron hydrochloride with five common parenteral drugs during simulated Y-site administration" vol. 65, No. 18, Sep. 15, 2008, p. 1735-1759.
European Patent Office, Extended European search report of EP 14873209.2, dated Jul. 5, 2017.
The 15th Revision of Japanese Pharmacopoeia (JP), issued on Apr. 25, 2006 & its English Translation of highlight related parts.
Transmission from Master of Drug formulation, 2nd vol, "Design of Parenteral administration formulation and preparation method therefor", issued on May 20, 2013 & its English Translation of highlight related parts.
Information for revision of attached document ALOXI® intravenous injection 0.75mg, Sep. 2012 & its English Translation of highlight related parts.
Trend about analysis of inorganic impurities in Pharmaceutical field, vol. 4, No. 21, Jun. 2013 & its English Translation of highlight related parts.
Chong Min Won et al., "Photolytic and oxidative degradation of an antiemetic agent, RG 12915", International Journal of Pharmaceutics 121 (1995) 95-105.
"The sixteenth (16th) revision, Manual of Japanese Pharmacopoeia", Monograph of medicaments, Tokyo Hirokawa Shoten, Jun. 2011 & its English Translation of related parts.
D.R. Lide et al., "Hand Book of Chemistry and Physics", 77th Edition, CRC Press Inc., 1996-1997.

\* cited by examiner

*Primary Examiner* — Sudhakar Katakam
(74) *Attorney, Agent, or Firm* — Lex IP Meister, PLLC

(57) ABSTRACT

Provided are a pharmaceutical composition with improved stability including palonosetron, a preparation method thereof, and a pharmaceutical package including the pharmaceutical composition.

5 Claims, No Drawings

PHARMACEUTICAL COMPOSITION CONTAINING PALONOSETRON

TECHNICAL FIELD

The present disclosure relates to a palonosetron-including pharmaceutical composition with improved stability, a preparation method thereof, and a pharmaceutical package including the pharmaceutical composition.

BACKGROUND ART

Administration of cancer chemotherapeutic agents including cisplatin induces nausea and vomiting in nearly all cases. Vomiting begins to occur 1 to 2 hours after administration of cisplatin, which is acute vomiting, and vomiting begins to subside by 18 to 24 hours. Then, vomiting begins to develop and peaks 48 to 71 hours, which is delayed vomiting.

Further, nausea and vomiting are the most common complications occurring after anesthesia and surgery. Postoperative vomiting may cause severe complications such as dehydration, electrolyte imbalance, gastric herniation, wound disruption, esophageal tears, muscular fatigue, etc., and it may increase anxiety about additional surgery in patients. In general, postoperative vomiting occurs within 24 hours after surgery in 25 to 40% of surgical patients.

Meanwhile, vomiting may be treated by antagonistic action of 5-HT3 (5-hydroxytryptamine) receptor antagonist at the cerebral functions related to 5-HT3 receptors.

The first-generation 5-HT3 receptor antagonist, ondansetron or granisetron is very effective for acute vomiting, but less effective in preventing delayed vomiting. Therefore, ondansetron or granisetron must be given intravenously once or more times before chemotherapy or radiotherapy is initiated. Thereafter, it must be given orally in a tablet or elixir form in order to prevent delayed vomiting. Because some anticancer chemotherapeutic agents can induce vomiting for a predetermined period of time or longer even when they are administered only once, a 5-HT3 antagonist must be administered every day until the risk of vomiting has substantially subsided.

U.S. Pat. No. 5,202,333 discloses an intravenous formulation of tricyclic 5-HT3 receptor antagonists including a bridged bicyclic amine substituent, such as palonosetron. This document discloses that an administration dose of the tricyclic 5-HT3 receptor antagonist generally ranges from 1 ng to 1 mg, preferably 10 to 100,000 ng per 1 kg of body weight. This document discloses a composition consisting of palonosetron hydrochloride, dextrose monohydrate, citric acid monohydrate, sodium hydroxide, and water for injection, but there is a problem that pharmaceutically acceptable storage stability was not secured.

Palonosetron hydrochloride is marketed under the brand name of ALOXI®. This product is a liquid formulation for single intravenous administration, available as a 5 mL single use vial or a 1.5 mL single use vial. Each 5 mL vial contains 0.25 mg of palonosetron, 207.5 mg of mannitol, citrate buffer, and disodium edetate. Each 1.5 mL vial contains 0.075 mg of palonosetron, 83 mg of mannitol, citrate buffer, and disodium edetate.

Korean Patent Nos. 10-1113084 and 10-1113087 disclose a pharmaceutically stable composition at pH of 4 to 6, including palonosetron, mannitol, citrate buffer, and 0.005 to 1.0 mg/ml of EDTA (ethylenediaminetetraacetic acid) as a chelating agent. In these documents, to secure stability of the pharmaceutically composition including palonosetron, disodium edetate or EDTA is used as a chelating agent. EDTA is used to treat acute and chronic lead poisoning by removing toxic elements including heavy metals such as lead, cadmium, and mercury from the blood stream (chelation therapy). EDTA chelation therapy is approved by the U.S. FDA for use in treating lead and heavy metal poisoning, and also used for emergency treatment of hypercalcemia and control of ventricular arrhythmias associated with digitalis toxicity. However, the most common side effect of EDTA is a burning sensation at the site of the injection, and some people may have an allergic reaction to EDTA. Other serious side effects that have been reported include low blood sugar, diminished calcium levels, headache, nausea, low blood pressure, kidney failure, organ damage, irregular heartbeat, seizures, or even death.

For pharmaceutically effective application of compositions including palonosetron, stability of palonosetron must be improved to secure a pharmaceutically available period. Therefore, a demand for a palonosetron formulation with pharmaceutically effective storage stability still remains.

DISCLOSURE

Technical Problem

Accordingly, an object of the present invention is to provide a pharmaceutical composition with improved palonosetron stability.

Another object of the present invention is to provide a pharmaceutical composition of palonosetron, of which long-term storage is possible by securing its pharmaceutically sufficient stability, and terminal sterilization is allowed.

Still another object of the present invention is to provide a liquid pharmaceutical composition including palonosetron and/or a pharmaceutically acceptable salt thereof, and an aqueous medium in the absence of a chelating agent such as disodium edentate, etc., and having improved palonosetron stability, and a preparation method thereof.

Technical Solution

An aspect of the present invention provides a pharmaceutical composition which includes one or more selected from the group consisting of palonosetron and pharmaceutically acceptable salts thereof as an active ingredient at a palonosetron concentration of 0.01 to 0.5 mg/ml in the absence of a chelating agent and maintains a total content of heavy metals to be equal to or less than 50 ppm for the duration of storage.

The pharmaceutical composition may further include a pharmaceutically acceptable aqueous carrier, and also further include a buffering agent, an isotonic agent, or a mixture thereof, in which pH of the composition may be preferably 4 to 6.

The pharmaceutical composition may be a liquid formulation or a lyophilized formulation for oral or parenteral administration, preferably, for parenteral administration.

Another aspect of the present invention provides a method of preparing the pharmaceutical composition which maintains a heavy metal content to be equal to or less than 50 ppm for the duration of storage, the method including the steps of:

preparing an aqueous solution including a buffering agent, an isotonic agent, or mixture thereof, and a pharmaceutically acceptable aqueous carrier;

treating the aqueous solution with a chelating resin to control the heavy metal content to be equal to or less than 50 ppm; and adding one or more selected from the group consisting of palonosetron and pharmaceutically acceptable salts thereof as an active ingredient to the aqueous solution or the aqueous solution of which heavy metal content is controlled.

In the method of preparing the pharmaceutical composition, the chelating resin may be directly contacted with the pharmaceutical composition or the pharmaceutical composition may be passed through a column packed with the chelating resin. The method of preparing the pharmaceutical composition according to an embodiment of the present invention may further include one or more steps selected from the group consisting of sterilization and lyophilization steps.

Still another aspect of the present invention provides a pharmaceutical package including a pharmaceutically acceptable container and the pharmaceutical composition including palonosetron and a pharmaceutically acceptable salt thereof as an active ingredient.

Best Mode

Hereinafter, the present invention will be described in more detail.

In an aspect of the present invention, provided is a pharmaceutical composition including one or more selected from the group consisting of palonosetron and pharmaceutically acceptable salts thereof as an active ingredient.

Palonosetron is a tricyclic 5-HT3 receptor antagonist used as an anti-emetic, and has prophylactic and/or therapeutic effects on nausea and/or vomiting. In particular, palonosetron is useful as an anti-emetic against for vomiting that occurs after surgery, chemotherapy, and radiotherapy. Palonosetron has a chemical name of (3aS)-2-[(3S)-1-azabicyclo[2.2.2]oct-3-yl]-2,3,3a,4,5,6-hexahydro-1H-benz[de]isoquinolin-1-one ($C_{19}H_{24}N_2O$) and a molecular weight of 296.407 g/mol, and has the following structure.

[Chemical Formula 1]

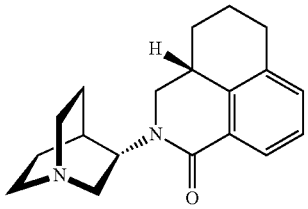

Of them, palonosetron hydrochloride has a chemical name of (3aS)-2-[(S)-1-azabicyclo[2.2.2]oct-3-yl]-2,3,3a,4,5,6-hexahydro-1-oxo-1H-benz[de]isoquinoline hydrochloride ($C_{19}H_{24}N_2O \cdot HCl$) and a molecular weight of 332.87 g/mol.

The palonosetron or pharmaceutically acceptable salt thereof is classified as a second-generation 5-HT3 receptor antagonist, and has a half-life of 40 hours or longer. Since the palonosetron or pharmaceutically acceptable salt thereof binds to 5-HT3 receptor for a long time to exhibit the effect for a long time, its inhibitory effect on delayed vomiting is 10 times higher than that of other first-generation 5-HT3 receptor antagonists, thereby being effectively applied to prevention and/or treatment of nausea and/or vomiting caused by chemotherapy such as cytotoxic anticancer agents, etc., radiotherapy, and/or surgery.

However, palonosetron has very poor stability, because it is easily oxidized and degraded by light or oxygen in a liquid medium. Therefore, it is necessary to secure stability of the drug. In particular, oxidation is known to be further accelerated by heavy metals present in the liquid medium, such as barium, manganese, zinc, copper, iron, lead, nickel or chromium. The heavy metals may be intermixed in palonosetron itself, or intermixed from an excipient such as a buffering agent or an isotonic agent which is added during preparation of the liquid formulation. The heavy metals may be also intermixed during preparation processes such as dissolution, filling, packaging, etc.

Therefore, in order to effectively prevent oxidation of the active ingredient palonosetron and/or oxidation accelerated by a trace amount of the heavy metals, it is necessary to remove a trace of the heavy metals or to prevent intermixing of the heavy metals.

Examples of the heavy metal may include one or more selected from the group consisting of barium, manganese, zinc, copper, iron, lead, nickel, and chromium.

In the pharmaceutical composition including palonosetron of an embodiment of the present invention, a palonosetron aqueous solution or an excipient aqueous solution excluding palonosetron is treated with a chelating resin to reduce the content of the heavy metals. Accordingly, the content of the heavy metals is controlled within an appropriate range, thereby improving storage stability of a palonosetron-containing formulation and also preparing an anti-emetic showing stable effects on delayed vomiting as well as acute vomiting.

In an embodiment of the present invention, the pharmaceutical composition including palonosetron may include heavy metals of 50 ppm or less, and more preferably, 10 ppm or less, during a pharmaceutically significant storage period.

The pharmaceutical composition including palonosetron, in which the content of heavy metals is controlled according to the present invention, may be stably stored for a long period of time without a chelating agent, for example, it may be stably maintained at room temperature for 2 years or longer. Specifically, the pharmaceutical composition according to the present invention may have storage stability of maintaining the content of palonosetron or a pharmaceutically acceptable salt thereof, for example, palonosetron hydrochloride at 95% by weight to 100% by weight of the initial content thereof, even when the pharmaceutical composition is stored at 25° C. for 24 months.

The pharmaceutical composition according to the present invention may include one or more selected from the group consisting of palonosetron and pharmaceutically acceptable salts thereof as an active ingredient, and a pharmaceutically acceptable aqueous carrier and/or a buffering agent, an isotonic agent, or a mixture thereof.

In an embodiment of the present invention, to effectively obtain the desired effects, a concentration of the active ingredient palonosetron may be 0.01 mg/ml to 0.5 mg/ml, 0.03 mg/ml to 0.2 mg/ml, 0.04 mg/ml to 0.07 mg/ml, or about 0.05 mg/ml.

The pharmaceutically acceptable salt of palonosetron may be a pharmaceutically acceptable salt and a salt possessing the desired pharmacological activity, and the salts may include acid addition salts formed with inorganic acids such as hydrochloric acid, bromic acid, sulfuric acid, nitric acid, phosphoric acid, etc.; or organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, etc.

pH of the pharmaceutical composition according to the present invention may be 4 to 6, preferably 4.5 to 5.5, for example, 5. To more stably maintain the pH range of the composition, an organic acid buffering agent such as citric acid and a salt of citric acid may be used. The buffering agent may be an organic acid buffering agent having excellent buffering capacity. The content of the buffer agent, in the case of a citrate buffering agent, may be 10 mM to 100 mM, based on the total pharmaceutical composition. The citrate buffering agent may be used at a concentration of preferably 10 to 40 mM, and more preferably, 15 to 30 mM, based on the total pharmaceutical composition.

The isotonic agent may be one or more selected from the group consisting of mannitol, lactose, dextrose, and trehalose, and preferably, mannitol. Mannitol may be included in an amount of 10 to 80 mg/ml, preferably 20 to 60 mg/ml, and more preferably 40 to 45 mg/ml, based on the total pharmaceutical composition.

In an embodiment of the present invention, the composition may be a liquid injectable formulation. If the palonosetron formulation according to the present invention is a liquid injectable formulation, it may be a sterile formulation or a lyophilized formulation which is obtained by performing one or more steps of sterilizing and lyophilizing the formulation having the controlled heavy metal content. Both of the two formulations must be prepared in a liquid form for intravenous administration, and therefore, the composition is advantageous in that its stability is maintained for a sufficient time even after preparation of the liquid formulation.

In another aspect of the present invention, provided is a method of preparing the pharmaceutical composition, in which the pharmaceutical composition includes one or more selected from the group consisting of palonosetron and pharmaceutically acceptable salts thereof as an active ingredient at a palonosetron concentration of 0.01 to 0.5 mg/ml, and the content of heavy metals is 50 ppm or less, in order to reduce the content of heavy metals for the improvement of stability of the palonosetron formulation. The preparation method may be performed by treating a palonosetron aqueous solution or an excipient aqueous solution including a buffering agent and an isotonic agent excluding palonosetron with a chelating resin.

Specifically, in an embodiment of the present invention, provided is a method of preparing the pharmaceutical composition having the content of heavy metals to be equal to or less than 50 ppm, the method including the steps of preparing the excipient aqueous solution including a buffering agent, an isotonic agent, or a mixture thereof and a pharmaceutically acceptable aqueous carrier; treating the excipient aqueous solution with the chelating resin to control the content of heavy metals to be equal to or less than 50 ppm; adding one or more selected from the group consisting of palonosetron and pharmaceutically acceptable salts thereof as an active ingredient to the excipient aqueous solution having the controlled heavy metal content.

Further, in an embodiment of the present invention, provided is a method of preparing the pharmaceutical composition having the content of heavy metal to be equal to or less than 50 ppm, the method including the steps of preparing a composition including a buffering agent, an isotonic agent, or a mixture thereof, and a pharmaceutically acceptable aqueous carrier, and one or more selected from the group consisting of palonosetron and pharmaceutically acceptable salts thereof; treating the composition with the chelating resin to control the content of heavy metals to be equal to or less than 50 ppm.

In the preparation method, treatment of the chelating resin may be performed by directly contacting with the chelating resin or passing through a column packed with the chelating resin. The chelating resin may include imidodiacetate and polyamine as substituents to form a chelate bond with heavy metals, thereby effectively removing heavy metals. Examples of the chelating resin may include commercially available DIAION CR11 (Mitsubishi, Co.), DIAION CR20 (Mitsubishi, Co.), Eporous MX-8C (Samyang, Corp.), etc. DIAION CR11 is a styrene-based porous chelating resin to remove metal ions by chelation of exchange groups with metal ions, and shows higher selectivity than strong or weak acid cation exchange resins for divalent ions such as zinc, copper, iron, etc. DIAION CR20 is a styrene-based porous chelating resin which has high selectivity for heavy metals, but does not adsorb alkali metal ions and alkali earth metal ions. Eporus MX8C is a chelating resin that adsorbs general heavy metals such as lead, zinc, copper, nickel, chromium, etc., and has excellent chemical stability and durability, thereby being used in waste water treatment and other various fields. If necessary, the above mentioned chelating resins may be used in combination of two or more thereof.

The chelating resin treatment step may be performed by directly contacting the palonosetron aqueous solution or the excipient aqueous solution including the buffering agent and the isotonic agent except palonosetron with the chelating resin, or by passing it through a general column packed with the chelating resin.

When the column packed with the chelating resin is used, the size of the column, feeding amount, etc. may be controlled by a general method, in order to remove heavy metals from the aqueous solution. Accordingly, heavy metals derived from raw materials including palonosetron may be effectively removed. If the total amount of the heavy metals derived from raw materials including palonosetron is smaller than the amount restricted by the present invention, the treatment of the chelating resin may be omitted.

After preparation of the pharmaceutical composition having the controlled heavy metal content, one or more steps selected from the group consisting of sterilization and lyophilization steps may be additionally performed. In particular, if the composition of the present invention is prepared in an injectable formulation, the sterilization step may be further performed to prepare a liquid injectable formulation, or the sterilization and lyophilization steps may be performed to prepare a lyophilized product.

It is preferable to prevent additional intermixing of heavy metals in the pharmaceutical composition having the controlled heavy metal content according to the present invention. Specifically, a pharmaceutically acceptable primary packaging container may be used. For example, a plastic container, in which an amount of heavy metals leached from the container for the duration of storage is restricted, a glass container surface-treated with silicon, etc., or a glass container, in which an amount of heavy metals leached from the container is restricted, is preferably used. It is preferable that these conditions can be satisfied, if rubber stoppers for sealing are needed. The amount of heavy metals leached from the whole container is preferably 50 ppm or less.

According to an embodiment of the present invention, as the pharmaceutically acceptable primary packaging container, a glass tubing vial may be used.

The glass is a transparent borosilicate glass, in particular, a low-expansion borosilicate glass, satisfying ASTM (American Society for Testing and Materials) type 1, class A, USP (US Pharmacopoeia) type 1 Powdered Glass, USP Arsenic, EP (European Pharmacopoeia) type 1 Glass Grains (Test B), and EP Arsenic conditions.

The glass may include $SiO_2 \geq 80\%$, for example, 80~85%; $Al_2O_3 \leq 5\%$, for example, 1~5%; $Na_2O+K_2O \leq 5\%$, for example, 1~5%; $CaO+MgO<0.2\%$, for example, more than 0% and less than 0.2%; $B_2O_3 \geq 10\%$, for example, 10~15%; $Fe_2O_3<0.1\%$, for example, more than 0% and less than 0.1%, and may not include $BaO$, $ZnO$, $MnO_2$, $TiO_2$, $SO_3$. For example, the glass may include $SiO_2$ 81%, $Al_2O_3$ 2%, $Na_2O+K_2O$ 4%, $CaO+MgO<0.2\%$, $B_2O_3$ 13%, $Fe_2O_3<0.1\%$, and may not include $BaO$, $ZnO$, $MnO_2$, $TiO_2$, $SO_3$.

The glass may have a strain point of less than 510° C., preferably more than 500° C. and less than 510° C., and most preferably 505° C.; an annealing point of 550~570° C., preferably 555~565° C., and most preferably 560° C.; a softening point of 800~900° C., preferably 800~850° C., and most preferably 820° C.; a linear coefficient of expansion (0-300° C.) of $30\times10^{-7}$~$40\times10^{-7}$, preferably $30\times10^{-7}$~$35\times10^{-7}$, and most preferably $33\times10^{-7}$; and a density of 2.2~2.3 $g/cm^3$, preferably 2.2~2.25 $g/cm^3$, and most preferably 2.22 $g/cm^3$.

The glass container may have element extraction data of the following Table 1.

TABLE 1

| Glass type | Si | Al | Na | K | Ca | Mg | Fe | Ba | Zn | Ti |
|---|---|---|---|---|---|---|---|---|---|---|
| $SiO_2$ | 4.8 | <0.01 | 1.1 | <0.03 | 0.13 | 0.07 | <0.012 | <0.008 | <0.01 | <0.005 |

(Unit: ppm, after autoclave in high-purity water at 121° C. for 60 min in a 20-mL container)

The glass may satisfy one or more of the above properties, preferably, all of the properties.

The pharmaceutical composition according to the present invention may be stored and/or distributed before use, after being filled and sealed in a vial or an ampoule. The storage may be performed under aseptic (sterile) environments (e.g., a clean room). To prevent a photochemical reaction by direct sunlight and degradation and/or denaturation of active ingredients caused thereby in the vial or ampoule, a brown-colored container may be used or the vial or ampoule may be stored in the dark. For example, in case the liquid pharmaceutical composition is prepared in the form of a sterile injectable formulation, it may be filled and sealed in a vial or ampoule made of glass or plastic, and then stored and/or distributed under aseptic (sterile) environments (e.g., a clean room). Further, to prevent a photochemical reaction by direct sunlight, a brown-colored container may be used or the composition may be stored in the dark.

The formulation including palonosetron according to the present invention may be formulated in a variety of different forms for oral or parenteral administration. In a specific embodiment, the liquid pharmaceutical composition may be prepared in a variety of different formulations for oral, intravenous, intramuscular, transcutaneous, intranasal, subcutaneous, or topical administration. The liquid pharmaceutical composition may be prepared in a lyophilized product as well as in a liquid form. Water for injection which is generally used in the preparation of injectable formulations is used, a final volume is adjusted, and a final sterilization process is performed to prepare an aseptic (sterile) injectable formulation, for example, an aseptic injectable formulation for intravenous administration. In another embodiment, the injectable formulation may be a lyophilized formulation as well as a liquid injectable formulation, but is not limited thereto. The lyophilized formulation of the liquid pharmaceutical composition may be prepared by removing the aqueous medium from the liquid pharmaceutical composition, and may have a composition similar to or equivalent to that of the above described pharmaceutical composition including palonosetron.

Effect Of The Invention

A pharmaceutical composition including palonosetron and/or a pharmaceutically acceptable salt thereof of the present invention has pharmaceutically significant stability and thus its long-term storage is possible. Further, provided are a palonosetron formulation, of which terminal sterilization is allowed, a liquid pharmaceutical composition with improved palonosetron stability in the absence of a chelating agent such as disodium edentate, etc., and a preparation method thereof.

DETAILED DESCRIPTION OF THE EMBODIMENTS

The present invention will be described in more detail with reference to the following Examples. However, these Examples are for illustrative purposes only, and the invention is not intended to be limited by these Examples.

EXAMPLE 1

Preparation of Pharmaceutical Composition 1.1. Pretreatment of Chelating Resin 50 ml of a chelating resin (DIAION CR11) was taken and filled in a column, and the column was washed with 100 times volume of purified water. Then, 50 ml of 1N-hydrochloric acid was added thereto and left for 1 hour. Thereafter, the column was prepared by washing with 150 ml of purified water.

1.2. Preparation of Excipient Aqueous Solution 156 mg of citric acid, 370 mg of sodium citrate, and 4.15 g of mannitol were weighed and added to a mixing container which was processed to be safe from leaching of heavy metals, and then purified water for injection was added thereto to a final volume of 100 ml. Finally, a liquid mixture was prepared. The liquid mixture was passed through the pretreated chelating resin column to prepare an excipient aqueous solution.

1.3. Preparation and Filling of Palonosetron Aqueous Solution 5.6 mg of palonosetron hydrochloride was added to and dissolved in 100 ml of the excipient aqueous solution obtained in Example 1.2. The solution was filled in a glass vial, of which inner wall was coated with silicon, followed by sealing. The glass vial was subjected to steam sterilization at 121° C. for 30 minutes to complete terminal sterilization.

EXAMPLE 2

Component Analysis of Pharmaceutical Composition

The palonosetron aqueous injectable solution prepared in Example 1 was stored at 40° C. for 6 months, and then a stability test regarding changes in the content of palonosetron and production of related impurities was performed to examine production of insoluble materials and color changes with the naked eyes. Changes in the content of palonosetron and production of related impurities were analyzed by HPLC, and an increase in the heavy metal amount was analyzed by ICP.

(1) Analysis of Heavy Metal Content

Heavy metals to be analyzed were Fe, Cu, Mn, Pb and Zn.

Analysis was performed using ICP/AES (Inductively coupled plasma/Atomic Emission Spectrometer, model name: OPTIMA 5300DV, Perkin Elmer) under the following conditions.

<Instrumental Conditions>
RF Power: 1300 watts
Nebulizer Ar Flow: 0.65 L/min
Plasma Ar Flow: 15 L/min
Pump Flow rate: 1.5 mL/min
View Dist.: 15 mm
Read Delay time: 30 sec
Sample Pretreatment About 100 mg of the sample was accurately weighed using a microwave digestion system (model: Multiwave 3000, manufacturer: Anton Paar), and subjected to complete acid digestion for about 2 hours using an acid mixture of nitric acid (5 mL) and hydrogen peroxide (1 mL). Then, the sample was subjected to filtration, followed by finally massing up to 50 ml. All pretreatment procedures should be performed using a Teflon container (metal free), not a glass container, in order to avoid contamination.

Preparation of Standard Solution and Measurement

An inorganic element standard for ICP (Merck, USA) of 1,000 ppm was used as a standard solution, and diluted with an acid mixture (sample blank) which was pretreated in the same manner as the sample. Calibration curves of the corresponding concentrations were constructed, and then ICP test was performed. The test results are given in Table 1.

(2) HPLC Analysis of Unknown Related Impurities

In detail, HPLC analysis was performed under the following conditions.

1) Operation a. Detector: UV absorption spectrophotometer (measurement wavelength: 210 nm)

b. Column: Zorbax SB 5 µm, C8, 250×4.6 mm or equivalent or better column c. Column temperature: room temperature d. Mobile phase: 0.67 mL of trifluoroacetic acid was added to 1000 mL of a mixture of water and acetonitrile (72:18), followed by mixing and filtering (0.46 µm).

e. Flow rate: 1.0 mL/min f. Injection volume: 80 µL

2) Calculation $$\text{Content of each related impurity (\%)} = \text{Peak area of unknown related impurity in a test solution} / \text{Peak area of palonosetron hydrochloride in the test solution} \times 100 \quad \text{[Mathematical Equation 1]}$$

(3) HPLC Analysis of Known Related Impurities

The known related impurities to be analyzed include (2-[(S)-1-azabicyclo[2.2.2]oct-3-yl]-2,4,5,6,-tetrahydro-1H-benz[de]isoquinoline-1-one hydrochloride and (3aR)-2-[(S)-1-azabicyclo[2.2.2]oct-3yl]-2,3,3a,4,5,6-hexahydro-1-oxo-1H-benz[de]isoquinoline hydrochloride.

1) Operation a. Detector: UV absorption spectrophotometer (measurement wavelength: 238 nm)

b. Column: Chirobiotic V, 5 µm, 4.6×250 mm, Hewlett-Packard c. Mobile phase: a mixture of 20 mM/L ammonium acetate buffer (pH 6.0)/tetrahydrofuran (9:1)

d. Column temperature: 35° C.

e. Flow rate: 1.2 mL/min f. Injection volume: 200 µL

2) Calculation

The contents of respective related impurities are calculated by the following equation.

Relative response factor (RRF) of 2-[(S)-1-azabicyclo[2.2.2]oct-3-yl]-2,4,5,6,-tetrahydro-1H-benz[de]isoquinoline-1-one hydrochloride was determined, and RRF of other related impurity was regarded as 1.

RRF=RF of 2-[(S)-1-azabicyclo[2.2.2]oct-3-yl]-2,4,5,6,-tetrahydro-1H-benz[de]isoquinoline-1-one hydrochloride/ RF of (3aR)-2-[(S)-1-azabicyclo[2.2.2]oct-3yl]-2,3,3a,4,5,6-hexahydro-1-oxo-1H-benz[de]isoquinoline hydrochloride $$\text{Calibration curve: } As = M \times Cs \quad \text{[Mathematical Equation 2]}$$

$$X = \frac{At}{M} \times \frac{1}{RRF}$$

$$\text{Content of each related impurity (\%)} = \frac{At}{M} \times \frac{1}{RRF} \times \frac{100}{C}$$

As: Peak area of standard solution

Cp: Concentration of standard solution (mg/mL)

Cs: Practical concentration, considering the content of standard solution (mg/mL)

P: Content of diastereomer standard (%)

X: Concentration of related impurity in test solution (mg/mL)

At: Peak area of related impurity in test solution

RRF: Relative response factor

M: Slope of calibration curve

C: Concentration of palonosetron hydrochloride in test solution (mg/mL)

Total amount of related impurities (%)=related impurity of a) (%)+related impurity b) (%)

(4) Test of Content

Related impurities were analyzed according to (2) HPLC analysis of unknown related impurities, and the content of palonosetron hydrochloride was calculated by the following Equation.

Content of palonosetron ($C_{19}H_{24}N_2O$: 296.40) in about 1 ml (mg)=Amount of standard (mg)× Peak area of palonosetron hydrochloride in test solution/Peak area of palonosetron hydrochloride in standard solution×C/240× 0.8904    [Mathematical Equation 3]

C: Purity of palonosetron hydrochloride standard (%/100)

It was examined whether the known related impurities of palonosetron aqueous solution, 2-[(S)-1-azabicyclo[2.2.2]oct-3-yl]-2,4,5,6,-tetrahydro-1H-benz[de]isoquinoline-1-one hydrochloride and (3aR)-2-[(S)-1-azabicyclo[2.2.2]oct-3yl]-2,3,3a,4,5,6-hexahydro-1-oxo-1H-benz[de]isoquinoline hydrochloride, and unknown related impurities were increased or not.

(5) Examination of Insoluble Particle Production and Color Change

A light obscuration automatic particle counter (model name: PAMAS-SVSS) was used to examine production of insoluble particles, and color changes were examined with naked eyes.

COMPARATIVE EXAMPLE 1

5.6 mg of palonosetron hydrochloride and 24 mg of copper sulfate were added to and dissolved in 100 ml of the excipient aqueous solution prepared in Example 1.2. The solution was filled in a glass vial, followed by sealing. The glass vial was subjected to steam sterilization at 121° C. for 30 minutes to complete terminal sterilization.

For the prepared formulation, HLPC analysis was performed to examine changes in the palonosetron content and production of related impurities, and ICP analysis was performed to examine an increase in the heavy metal content, substantially in the same manner as in Example 2. The experimental results are summarized in Table 1.

COMPARATIVE EXAMPLE 2

156 mg of citric acid, 370 mg of sodium citrate, and 4.15 g of mannitol were weighed and added, and then purified water for injection was added thereto to a final volume of 100 ml. Finally, an excipient aqueous solution was prepared. Unlike Example 1, the solution was not passed through the chelating resin column.

5.6 mg of palonosetron hydrochloride was dissolved in 100 ml of the excipient aqueous solution thus prepared. The solution was filled in a glass vial, followed by sealing. The glass vial was subjected to steam sterilization at 121° C. for 30 minutes to complete terminal sterilization.

For the prepared formulation, HLPC analysis was performed to examine changes in the palonosetron content and production of related impurities, and ICP analysis was performed to examine an increase in the heavy metal content, substantially in the same manner as in Example 2. The experimental results are summarized in Tables 2 and 3.

TABLE 2

| | Example 1 | |
|---|---|---|
| Section | Immediately after preparation | storage for 6 months at 40° C. |
| Related impurities (wt %) | undetected | 0.10% |
| Unknown related impurities (wt %) | undetected | 0.10% |
| Total amount of related impurities (wt %) | undetected | 0.10% |
| Total amount of heavy metals (ppm) | undetected | undetected |
| Insoluble particles (in 1.5 ml) | 10 mcm or more: 18 particles 25 μm or more: 1 particles | 10 mcm or more: 16 particles 25 μm or more: 3 particles |
| Color | Colorless transparent | Colorless transparent |

TABLE 3

| | Comparative Example 1 | | Comparative Example 2 | |
|---|---|---|---|---|
| Section | Immediately after preparation | storage for 6 months at 40° C. | Immediately after preparation | storage for 6 months at 40° C. |
| Related impurities (wt %) | undetected | 1.30% | undetected | 1.30% |
| Unknown related impurities (wt %) | 0.50% | 3.50% | 0.50% | 3.50% |
| Total amount of related impurities (wt %) | undetected | 4.80% | undetected | 4.80% |
| Total amount of heavy metals (ppm) | 98 ppm | 120 ppm | 10 ppm | 60 ppm |
| Insoluble particles (in 1.5 ml) | 10 mcm or more: 15 particles 25 μm or more: 3 particles | 10 mcm or more: 17 particles 25 μm or more: 5 particles | 10 mcm or more: 18 particles 25 μm or more: 1 particle | 10 mcm or more: 18 particles 25 μm or more: 3 particles |
| Color | Colorless transparent | Colorless transparent | Colorless transparent | Colorless transparent |

In the tables, the related impurities are 2-[(S)-1-azabicyclo[2.2.2]oct-3-yl]-2,4,5,6-tetrahydro-1H-benz[de]isoquinoline-1-one hydrochloride and (3aR)-2-[(S)-1-azabicyclo[2.2.2]oct-3yl]-2,3,3a,4,5,6-hexahydro-1-oxo-1H-benz[de]isoquinoline hydrochloride.

Changes in the content of Example for a storage period of 6 months were in the range from 95 wt % to 110 wt % of the initial content, and the contents of all the related impurities were less than 1% and the total content of the related impurities was less than 2%. No heavy metals were detected upon preparation, and the total amount of heavy metals for the duration of storage was less than 10 ppm.

In Comparative Example 1 and Comparative Example 2, related impurities were continuously increased over time. In particular, in Comparative Example 1, respective related impurities were increased to 1% or more, and the total amount of the related impurities was 2% or more. In Comparative Example 1, the content of heavy metals was 100 ppm or more of copper ion, upon preparation.

EXAMPLE 3

(1) Sample Preparation

A sample was prepared according to the composition of the following Table 4.

TABLE 4

| Components | Composition 1 | Composition 2 |
| --- | --- | --- |
| Palonosetron hydrochloride | 0.056 mg | 0.056 mg |
| D-mannitol | 41.5 mg | 41.5 mg |
| Sodium citrate | 3.7 mg | 3.7 mg |
| Citric acid monohydrate | 1.56 mg | 1.56 mg |
| Glutamic acid | — | 3 mg |
| Water for injection | 1 ml | 1 ml |

(2) Storage Conditions and Period

The samples were sealed using an aluminum seal and a rubber septum, and left at 60° C. for 2~3 weeks after light was blocked out.

(3) Analysis Method

Analysis was performed by HPLC.

a) Preparation of Buffer 3.1 g of sodium dihydrogen orthophosphate and 2.5 mL of triethylamine were accurately weighed and added to a flask with a volume of 1000 mL, and dissolved in purified water to the marked line. pH of this solution was adjusted to 7.0±0.05 using phosphate. Before pH measurement, a pH meter was corrected by standard buffers of 1) 6.00 and 2) 8.00. Filtration was performed using a filter paper of 0.45 μm, followed by degassing.

b) Preparation of Mobile Phase A

The prepared buffer was used as a mobile phase A.

c) Preparation of Mobile Phase B

Acetonitrile was used as a mobile phase B.

*Caution: mobile phase was used within 16 hours after preparation.

d) Diluent

A solution was prepared by homogenously mixing the buffer and acetonitrile at a volume ratio of 50:50.

e) Chromatography Conditions

Column: 150 mm×4.6 mm, 5 μm, Intersil C8 or equivalent thereto

Column flow rate: 1.0 mL/min

Detector: UV wavelength: 210 nm

Feeding amount: 20 μl

Column temperature: 40° C.

Analysis time: 45 minutes

Gradient elution program: according to the following Table 5

TABLE 5

| Time (min) | Mobile phase A (%) | Mobile phase B (%) |
| --- | --- | --- |
| 0.01 | 80 | 20 |
| 2.0 | 80 | 20 |
| 25.0 | 65 | 35 |
| 35.0 | 65 | 35 |
| 37.0 | 80 | 20 |
| 45.0 | 80 | 20 | f) A total amount of unidentified related impurities (%)=A sum of peak areas of respective unidentified related impurities of test sample/a peak area of palonosetron of test sample×100

(4) Results

As shown in the following Table 6, solutions excluding EDTANa were filled and sealed in clear glass vials provided by manufacturers W and Y and plastic vials provided by Daikyo as primary packaging materials.

After being stored at 60° C. for 2 weeks, the total amount of the unidentified related impurities was examined. When the packaging material of the manufacturer W was used, the total amount of the unidentified related impurities was 0.1~0.3%, suggesting that this packaging material is more stable than other packaging materials.

TABLE 6

Total amount of unidentified related impurities (%) in the composition of the present invention according to packaging materials

| Manufacturer/sample | W*/composition 1 | W/composition 2 | Y**/composition 2 | Daikyo(CD)***/composition 1 |
| --- | --- | --- | --- | --- |
| Immediately after preparation | 0.1% | N.D. | N.D. | 0.1% |
| After storage at 60° C./2 weeks | 0.3% | 0.1% | 3.2% | 1.6% |

(*Packaging material of Manufacturer W: Wheaton Borosilicate Tubing Vial Clear Manufacturer Y: white pharmaceutical vial of Yeon Hap Glass Co., Ltd (Dealkalization treatment) *Daikyo: Daikyo Crystal Zenith vial)

The invention claimed is:

1. A pharmaceutical package, comprising:
a pharmaceutically acceptable container, and
a pharmaceutical composition comprising:
   palonosetron or pharmaceutically acceptable salts thereof in the container as an active ingredient at a concentration of 0.01 to 0.5 mg/ml;
   a pharmaceutically acceptable aqueous carrier;
   a buffering agent, an isotonic agent, or a mixture thereof,
wherein the pharmaceutically acceptable container is a transparent borosilicate glass container, and the glass is a low-expansion borosilicate glass, satisfying ASTM type 1, class A, USP type 1 Powdered Glass, USP Arsenic, EP type 1 Glass Grains (Test B) and EP Arsenic conditions, and
wherein the pH of the pharmaceutical composition is 4 to 6,
wherein the pharmaceutical composition is free of EDTA or a salt thereof,
wherein a total content of heavy metals is maintained to be equal to or less than 50 ppm during a storage period, and
wherein the pharmaceutical composition has storage stability of maintaining the content of palonosetron or a pharmaceutically acceptable salt thereof at 95% by weight to 100% by weight based on the initial content thereof when the pharmaceutical composition is stored at 25 ° C. for 24 months.

2. The pharmaceutical package of claim 1, wherein the pharmaceutically acceptable container is a glass tubing vial.

3. The pharmaceutical package of claim 1, wherein the glass satisfies the following conditions:
   1) a strain point of less than 510° C.,
   2) an annealing point of 550 to 570° C.,
   3) a softening point of 800 to 900° C.,
   4) a linear coefficient of expansion (0-300 ° C.) of $30 \times 10^{-7}$ to $40 \times 10^{-7}$, and
   5) a density of 2.2 to 2.3 g/cm$^3$.

4. The pharmaceutical package of claim 1, wherein the glass comprises SiO$_2$≥80%, Al$_2$O$_3$≤5%, Na$_2$O+K$_2$O≤5%, CaO+MgO<0.2%, B$_2$O$_3$≥10% and Fe$_2$O$_3$<0.1%, and does not comprises BaO, ZnO, MnO$_2$, TiO$_2$, and SO$_3$.

5. The pharmaceutical package of claim 1, wherein the glass container has element extraction data of the following table:

| Glass type | Si | Al | Na | K | Ca | Mg | Fe | Ba | Zn | Ti |
|---|---|---|---|---|---|---|---|---|---|---|
| SiO$_2$ | 4.8 | <0.01 | 1.1 | <0.03 | 0.13 | 0.07 | <0.012 | <0.008 | <0.01 | <0.005 |

(unit: ppm, after autoclave in high-purity water at 121° C. for 60 min in a 20-mL container).

\* \* \* \* \*